United States Patent [19]

Tada

[11] Patent Number: 5,580,975
[45] Date of Patent: Dec. 3, 1996

[54] AGENT FOR KEEPING CUT FLOWERS FRESH

[75] Inventor: Suguru Tada, Marugame, Japan

[73] Assignee: OD Kikaku Co., Limited, Kagawa-ken, Japan

[21] Appl. No.: 276,726

[22] Filed: Jul. 18, 1994

[30] Foreign Application Priority Data

Jul. 23, 1993 [JP] Japan ................................. 5-182558

[51] Int. Cl.$^6$ .............................. C07H 3/00; C08B 37/00
[52] U.S. Cl. ................................. 536/123; 536/123.1
[58] Field of Search ................................. 536/114, 123, 536/123.1

[56] References Cited

U.S. PATENT DOCUMENTS

| | | | |
|---|---|---|---|
| 4,326,052 | 4/1982 | Kang et al. | 536/123 |
| 4,385,123 | 5/1983 | Kang et al. | 435/101 |
| 4,503,084 | 3/1985 | Baird et al. | 426/573 |
| 4,517,216 | 5/1985 | Shim | 536/114 |
| 4,935,447 | 6/1990 | Philips et al. | 514/640 |
| 4,958,016 | 9/1990 | Kerkenaar et al. | 536/123 |

OTHER PUBLICATIONS

Carbohydrate Research, vol. 124, Issued 1983, O'Neill et al, "Structure of the Acidic Extracellular Gelling Polysaccharide Produced by *Pseudomonas Elodea*", pp. 123–133.

Carbohydrate Research, vol. 206, Issued 1990, O'Neill et al, "Structural Analysis of an Acidic Polysaccharide Secreted by Xanthobacter Sp. (ATCC 53272)", pp. 289–296.

*Primary Examiner*—John Kight
*Assistant Examiner*—Everett White
*Attorney, Agent, or Firm*—Keck, Mahin & Cate

[57] ABSTRACT

An agent for keeping cut flowers fresh contains a polysaccharide gel, such as gellan gum, dispersed at a concentration of 0.05 wt. % to 1.50 wt. %, into water, and gelatinized. The resultant polysaccharide gel has a gel strength of 50 to 7000×10$^3$ dyn/cm$^2$. A method for preserving cut flowers using gellan gum and a method for transporting cut flowers having cut stems inserted into the gellan gum are also described.

14 Claims, 3 Drawing Sheets

AGENT FOR KEEPING CUT FLOWERS FRESH

BACKGROUND OF THE INVENTION

1. Field of the Invention

The present invention relates to a method of preserving cut flowers in a fresh state, a method for transporting cut flowers kept in a fresh state to remote locations, and an agent for keeping cut flowers fresh.

2. Description of the Prior Art

In transporting cut flowers, by convention, the stems of the cut flowers are inserted in a water-impregnated foam of phenolic resin, for example.

During the transportation of the cut flowers by transporting means, such air planes or tracks, water is frequently leaked from the phenolic resin foam. An insufficient amount of water is supplied to the cut flowers. The cut flowers are droop and lose their value as commodities.

The phenolic resin foam has such nature that it does not decay and is hard to break up, and generates a bad smell and a dense cloud of black smoke when it is burnt. Because of this, it is difficult to dispose of the waste phenolic resin foam. As a result, additional labor for the disposal of the phenolic resin foam after used, increase of cost, additional space for temporarily storing the used foam are required by those persons engaging in the natural flower business, such as flower growers, flower merchants, and flower consumers.

SUMMARY OF THE INVENTION

Accordingly, objects of the present invention are to provide a method of transporting cut flowers which succeeds in solving the problems of water leakage resulting from the rolling and tilting which the cut flowers experienced during their transportation, difficulty of disposal of the used foam, and the like, and transportation of fresh cut flowers to domestic locations and overseas locations in an inexpensive manner, a method for preserving cut flowers in a fresh state, and an agent for keeping cut flowers fresh.

The above objects, are achieved by the subject invention of a novel and unique method for transporting cut flowers in a fresh state, a method for preserving cut flowers in a fresh state, and an agent for keeping cut flowers fresh.

An agent for keeping cut flowers fresh is prepared in a manner that polysaccharide, which is formed by polymerizing units of →3)-β-D-glucopyranose (Glcp)-(1→4)-β-D glucuronic acid (GlcpA)-(1→4)-β-D-glucopyranose (Glcp)-(1→4)-α-L-rhamnopyranose (Rhap)-(1→, is dispersed, at a concentration of 0.05 wt. % to 1.50 wt. %, into water, thereby to be gelatinized, and hence the resultant polysaccharide gel has a gel strength of 50 to 7000×10$^3$ dyn/cm$^2$.

The polysaccharide gel has a good syneresis. Because of this, if the cut end of the cut flower is inserted into the polysaccharide gel, water can be supplied to the cut flower. If the gel strength of the polysaccharide gel is properly selected, the cut flowers can be kept upright. Accordingly, water can be supplied to the upright cut flower. Thus, the freshness keeping agent is suitable for the transportation of a batch of cut flowers. Particularly when the freshness keeping agent is used for such transportation where the cut flowers constantly undergo great rolling and tilting, possibly causing liquid out of the liquid supply means, for example, transportation by air plane, overland transportation, and marine transportation, there is no danger of liquid outflow because the polysaccharide gel is used for the water supply means. Water is less evaporated from the gel surface. Thus, a batch of cut flowers can be transported without damaging them while water is satisfactorily supplied to the cut flowers. The polysaccharide gel may be easily destroyed, allows water to easily be supplied therefrom, and is not poisonous. Therefore, the polysaccharide gel after use can be thrown away without apprehension.

When the concentration of the gellan gum is set in the range of 0.15 wt. % to 0.50 wt. %, the gel strength thereof is adjusted to be within the range between 100 to 1000×10$^3$ dyn/cm$^2$, and a more effective freshness keeping agent is secured.

A method of preserving cut flowers in a fresh state is characterized in that polysaccharide, which is formed by polymerizing units of →3)-β-D-glucopyranose (Glcp)-(1→4)-β-D-glucuronic acid (GlcpA)-(1→4)-β-(D-glucopyranose (Glcp)-(1→4)-α-L-rhamnopyranose (Rhap)-(1→, is dispersed, at the concentration of 0.05 wt. % to 1.50 wt. %, into water, thereby to have polysaccharide gel of 50 to 7000×10$^3$ dyn/cm$^2$ in breaking stress, a hydrophobic bag and/or container is filled with the thus prepared polysaccharide gel, and the cut ends of the cut flowers are inserted, for preservation, into the polysaccharide gel contained.

In the method for preserving cut flowers in a fresh state, when a hydrophobic bag and/or container is filled with the polysaccharide gel adjusted such that the concentration thereof is set within the range from 0.15 wt. % to 0.50 wt. %, the breaking stress thereof is set within a range between 100 to 1000×10$^3$ dyn/cm$^2$. Under this condition, the cut ends of the cut flowers may be inserted in the polysaccharide gel contained in the bag and/or container, water is easily absorbed by the cut flowers and the cut flowers can be preserved fresh more reliably.

A method of transporting cut flowers in a fresh state is characterized in that polysaccharide, which is formed by polymerizing units of →3)-β-D-glucopyranose (Glcp)-(1→4)-β-D-glucuronic acid (GlcpA)-(1→4)-β -D-glucopyranose (Glcp)-(1→4)-α-L-rhamnopyranose (Rhap)-(1→, is dispersed, at the concentration of 0.05 wt. % to 1.50 wt. % into water, thereby to be gelatinized, and hence the resultant polysaccharide gel has a gel strength of 50 to 7000×10$^3$ dyn/cm$^2$, a hydrophobic bag and/or container is filled with the polysaccharide gel, the cut ends of the cut flowers are inserted into the polysaccharide gel contained therein, and the cut flowers are transported in this state.

In the method for transporting cut flowers in a fresh state, when a hydrophobic bag and/or container is filled with the polysaccharide gel adjusted such that the concentration thereof is set within the range from 0.15 wt. % to 0.50 wt. %, and hence the breaking thereof is set within a range between 100 to 1000×10$^3$ dyn/cm$^2$, the cut ends of the cut flowers are inserted in the polysaccharide gel contained therein, and the cut flowers are transported in this state, the cut flowers can be more reliably transported to remote locations while keeping the cut flowers fresh.

DETAILED DESCRIPTION OF THE PREFERRED EMBODIMENTS

A method for preserving cut flowers in a fresh state, a method for transporting cut flowers in a fresh state, and an agent for keeping cut flowers fresh according to the present invention will be described with reference to the accompanying drawings.

Figure 1:
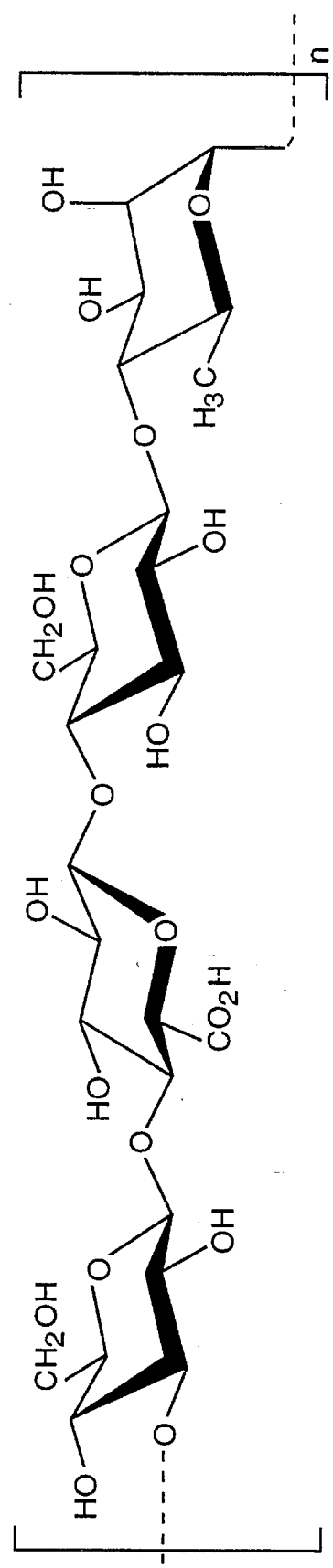
FIG. 1 shows a molecular structural formula for a polysaccharide gel of the invention.

An agent for keeping cut flowers fresh consists of polysaccharide gel. The polysaccharide gel, as expressed by a structural formula shown in FIG. 1, is formed by polymerizing units of $\rightarrow$3)-β-D-glucopyranose (Glcp)-(1$\rightarrow$4)-β-D-glucuronic acid (GlcpA)-(1$\rightarrow$4)-β-D-glucopyranose (Glcp)-(1$\rightarrow$4)-α-L-rhamnopyranose (Rhap)-(1$\rightarrow$. This polysaccharide gel is generally called a gellan gum.

The dispersion medium of the gellan gum is water. The concentration of the gellan gum is within the range of 0.05 wt. % to 1.50 wt. % in the dispersion medium. The gel strength of the gellan gum is within the range of 50 to 7000×10$^3$ dyn/cm$^2$. When the gel strength of the gellan gum is 50×10$^3$ dyn/cm$^2$ or smaller, the ability of the gel to maintain its shape is weak, so that the gel cannot hold cut flowers in an upright state. When the strength thereof is 7000×10$^3$ dyn/cm$^2$ or larger, the gel is too hard to insert the cut flowers thereinto. When the concentration of the gellan gum is set within the range of 0.15 wt. % to 0.50 wt. %, the gel strength thereof is adjusted to be within the range of 100 to 1000×10$^3$ dyn/cm$^2$. Under this condition, the gel can stably hold the erect cut flowers and further supply of water to a cut flower through its cut end is allowed.

When the concentration of the gellan gum is too low, the gel is easily destroyed, so that it cannot hold the cut flower in an upright position. Conversely, when the concentration of the gellan gum is too high, the gel is too hard, so that it rejects the insertion of the cut flower thereinto. Accordingly, the concentration of the gel must be selected to be within a proper range of the values of concentration. When the concentration of the gellan gum is set within the range of 0.15 wt. % to 0.50 wt. %, a gel strength of 100 to 1000×10$^3$ dyn/cm$^2$, which is high enough to stably hold the cut flowers erect, can be obtained.

Gelatinization promoting calcium salts, plant life prolonging agent, and the like are selectively dispersed in the dispersion medium, in addition to the gellan gum.

The calcium salts for gelatinization promotion are water soluble. When the concentration of the salts in the gellan gum gel is decreased, the breaking stress becomes low. The breaking stress becomes low also when the concentration of the calcium salts is too high. After the gellan gum is dispersed into water, the calcium salts are dispersed into the resultant water solution. The effective concentration of calcium ions of the calcium salts is within 0.001 wt. % to 0.10 wt. % in the gellan gum water solution, preferably 0.007 wt. % to 0.05 wt. %. The gelatinization promotion material may be any of metal salts having a valence of 2, such as calcium, magnesium, and manganese, metal salts having a valence of 1, such as sodium and potassium, organic and inorganic acids, and material containing any of those metal salts. The quantity of the plant life prolonging agent added to the dispersion medium is properly selected in accordance with the kind and the use of the cut flowers. The plant life prolonging agents may be bactericide, e.g., 8-hydroxy quinoline salt, nutrient, e.g., glucose, such anti-ethylene agent as STS, water clarifying agent, e.g., aluminum sulfate, growth regulators such as GA$^3$, BA, ABA, and NAA, physiological activating agent, e.g., vitamin, polysaccharide, and the like.

The polysaccharide other than the gellan gum is used for restricting water absorption by cut flowers and hence the florescence of the cut flowers, and an excessive supplying of water. To this end, it is necessary to add a very small quantity of these polysaccharides to the dispersion medium.

The polysaccharide to be additionally added may be starch, cellulose, sodium alginate, carrageenan, gluconic mannan, agar, pectin, pullulan, chitin, chitosan, xanthan gum, guar gum, locust bean gum, gum arabic, or tamarind seed polysaccharide. This polysaccharide may be substituted by protein, such as bean protein, gluten, gelatin, and collagen, or polyvalent alcohol. The polysaccharide, protein, or alcohol to be additionally added must be selected from among those not bindering the gelatinization of the polysaccharide. The concentration of the additive material is lower than 0.1 wt. %, preferably within 0.05 wt. % to 0 wt. %.

Since the gellan gum thus prepared is excellent in syneresis, it allows a cut flower to smoothly absorb water through its cut end. Since this gellan gum has a proper gel strength, it can keep its shape and does not drop out of the container if it undergoes tilting and rolling during the transportation of the cut flowers. Less water is evaporated from the gel surface since its surface area hardly varies. Additionally, the gellan gum can stably hold the cut flowers in an upright state, so that the cut flowers will not be damaged by their falling down.

Thus, the freshness keeping agent is suitable for the preservation of the cut flowers in a fresh state, and for such a transportation where the cut flowers constantly undergoes great rolling and tilting for example, transportation by air plane, overland transportation, and marine transportation. Accordingly, the transporting means can transport the cut flowers at high speed, without any apprehension of shaking.

Since the gellan gum gel contains bactericide, nutrient, e.g., glucose, anti-ethylene agent, growth regulators, and the like, the freshness of the cut flowers can be preserved for a long time. Accordingly, when the cut flowers are transported while inserted in the gellan gum gel and placed in properly set temperature, humidity and brightness, the fresh cut flowers can be delivered to customers overseas. There are many kinds of cut flowers, such as bunches of flowers for various types of ceremonies. The amount of the gellan gum gel to be contained is several cc to several thousands cc, for example.

A method of preparing the gellan gum gel for the cut-flower freshness keeping agent will be described.

Figure 2:
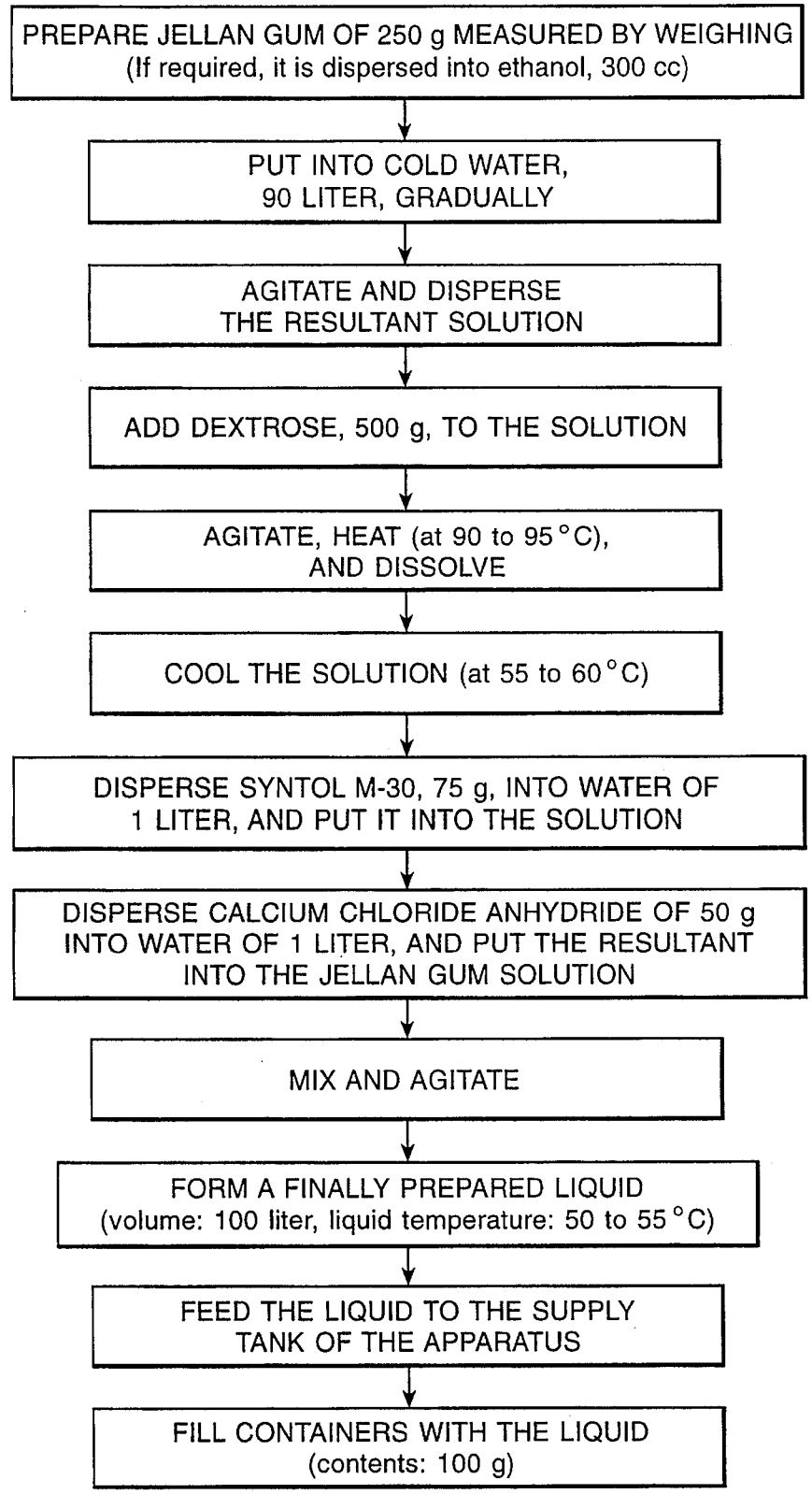
FIG. 2 is a chart showing a process of preparing gellan gum gel.

As shown in a process chart of FIG. 2, gellan gum of 250 g is gradually put into cold water of 90 liter and dispersed while agitating it. If required, it is preparatorily dispersed in ethanol of 300 ml. The dispersed gellan gum solution is dissolved at 90° C. to 95° C. The heated gellan gum solution is cooled after being dissolved. Before the gellan gum solution is cooled to 60° C., glucose solution prepared by preparatorily dispersing glucose of 500 g into water is put into the gellan gum solution. After the gellan gum solution is cooled to 55° C. to 60° C. or lower, antimicrobial agent, which is prepared by dispersing syntol(thiabenzol: antifungal agent) of 50 g to 150 g into water of 1 liter, is put into the cooled gellan gum solution, a gelatinization promotion agent formed by dispersing calcium chloride of 50 g into water of 1 liter is put into the gellan gum solution, and then the plant life prolonging agent is put into the resultant solution. The gellan gum solution is then mixed, and the solution of 100 liter and at 50° C. to 55° C. in liquid temperature is kept hot as the finally prepared liquid, and fed to a liquid supply tank of a liquid filling apparatus before it is gelatinized. Then, bags or containers for storage or transportation are filled with the gellan gum solution by using the filling apparatus, and the solution is gelatinized in the hydrophobic bags or containers.

Methods of preserving and transporting cut flowers in a fresh state by using the gellan gum will be described.

To preserve the cut flowers and/or plants with the gellan gum, a container or bag made of polyvinyl chloride, polyethylene, polyester, polypropylene, or the like is filled with the not-gelatinized gellan gum from the filling apparatus. In this case, when the height of the gellan gum solution from the bottom to the liquid level is selected to be 50% to 150% of the width of the bottom of the container, the container is stably set. Preferably, the height of the gellan gum solution from the bottom to the liquid level is selected within 50% to 150% of the width of the bottom of the container. If so selected, the container will not fall down. Alternatively, a polyethylene bag is laid out or set in a paper or plastic container. The gellan gum solution before gelatinization is put into the bag and gelatinized, and then cut flowers are inserted in the gellan gum gel. In this case, the amount of the gellan gum gel is determined by the shape and size of the cross section of the cut flowers, the size, type, and number of the cut flower, and the number of days for preservation. Our experimental data shows that when a number of cut flowers such as 3 to 20 cut flowers are preserved at 20° C. for 5 days, the amount of gellan gum gel is approximately 50 g to 300 g.

The bag for containing the gellan gum gel, after it contains the gel, may take any suitable shape, such as tubular shapes, and well designed shapes. The hydrophobic container may be a tubular plastic container, or a container made of foamed styrol. In this case, the container may be used repeatedly. When a container is a paper box and a polyethylene bag is set in the paper box, and the gellan gum gel is put into the bag, the paper bag can be easily thrown away after the flowers are used. The gellan gum gel after transportation will be decayed with time after water is exuded therefrom.

EXPERIMENT 1

Figure 3:
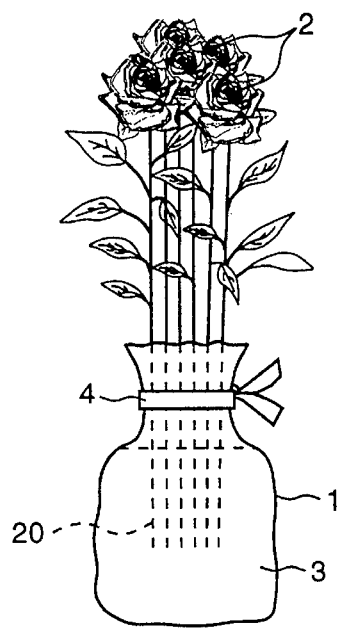
FIG. 3 is a diagram showing cut flowers being planted in the gellan gum gel contained in a container.

Example 1 of the gellan gum will be described with reference to FIG. 3.

Gellan gum of 3 g and a plant life prolonging agent of 10 g were put into a breaker 11. Cold water of about 950 cc was additionally put thereinto, and heated at 90° to 95° C. for 30 minutes while agitating the resultant solution. In this way, gellan gum solution was prepared. Water solution of 20 cc containing calcium chloride of 0.5 g was added to the gellan gum solution and agitated. Further, water was added thereto, thereby to prepare gellan gum solution of 1000 cc. The solution was cooled to 50° to 55° C. while agitating it. And it was kept at 50° C. so as to prevent the gelatinization of the gellan gum solution.

Subsequently, gellan gum solution in an amount of 500 cc was put into a polyvinyl chloride bag 1 of 1500 cc in contents, and cooled to be gelatinized. Ten cut flowers 2 were inserted in the gellan gum after being gelatinized and cooled at normal temperature. Then, the opening of the bag 1 was closed using a tape 4.

The cut flowers thus inserted in the gellan gum gel were placed at room temperature in the shade, and observed with the naked eye over 24 to 72 hours. The result was that the cut flowers were kept fresh without any deterioration of the quality of the cut flowers.

EXAMPLE 2

Figure 4:
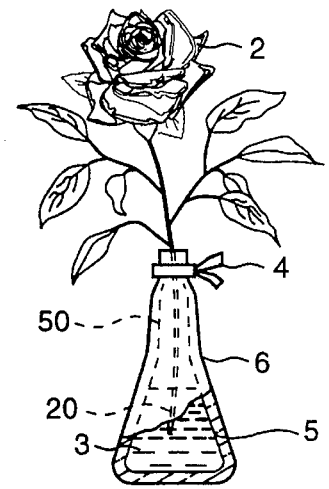
FIG. 4 is a diagram showing cut flowers being planted in the gellan gum gel contained in a breaker.

Example 2 is shown in FIG. 4. In Example 2, the gellan gum solution of 20 cc. prepared in Example 1, was put into a triangle-flask shaped plastic vase 5 of 30 cc, and cooled to be gelatinized. One cut flower was inserted into the gellan gum gel in the vase. The space between the stem of the cut flower and the circumferential edge of the opening of the vase was closed using cellophane 6 and tape 4.

The cut flower 2 thus inserted was placed at room temperature in the shade, and observed with the naked eye over 24 to 72 hours. The result was that the cut flower was kept fresh without any deterioration of the quality of the cut flower. A vase with one flower could be obtained merely by unpacking. The container fell down, but neither the gellan gum gel or water were flowed out, and the supply of water to the flower was continued.

EXAMPLE 3

Figure 5:
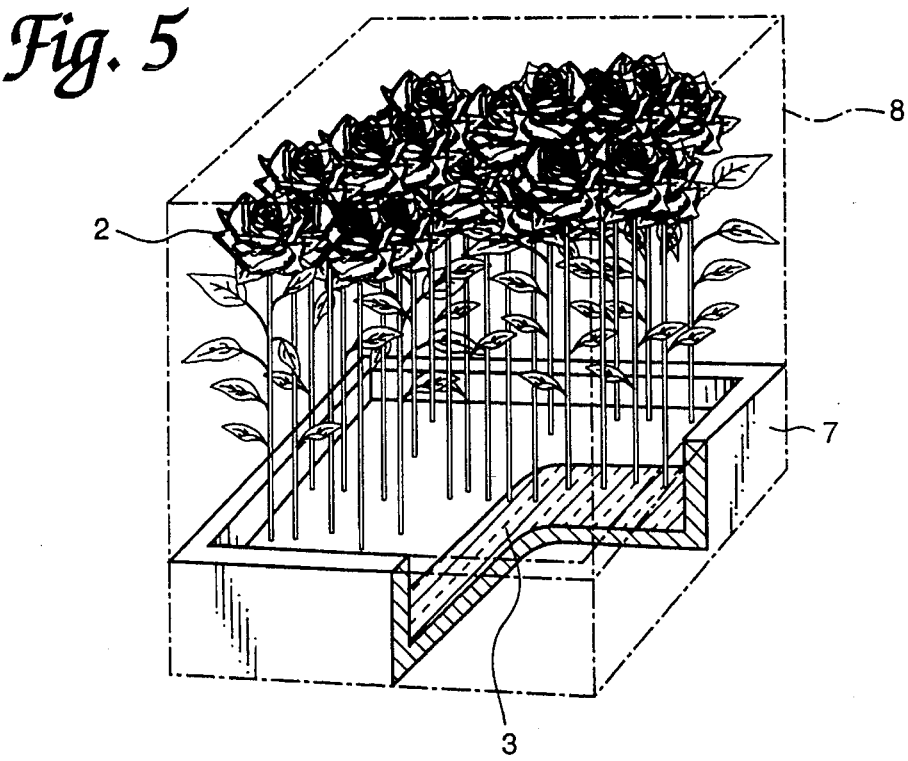
FIG. 5 is a diagram showing cut flowers being planted in the gellan gum gel contained in a box.

FIG. 5 illustrates Example 3. In this example, a container 7 used was made of foamed styrol and had the size of 35 cm in height, 50 cm in width, and 15 cm in depth. The gellan gum solution, prepared in Example 1, was put into the container 7, up to the liquid level of 10 cm. The solution was cooled to normal temperature to be gelatinized. Flowers gathered from a garden were inserted in the full area of the surface of the gellan gum gel in the container 7. The container 7 was packed in a corrugated cardboard container ready for delivering.

The cut flowers thus planted were placed at room temperature in the shade, and observed with the naked eye over 24 to 72 hours. The result was that the cut flowers were kept fresh without any deterioration of the quality of the cut flowers.

As seen from the foregoing description, since the freshness keeping agent of the invention consists of gellan gum gel, it has a good syneresis. Because of this, it can supply a satisfactory amount of water and nutritive substance to the cut flowers inserted thereinto. Further, it has a proper gel strength. Because of this, when it is shaken, the gel surface is moved less than a liquid surface. Therefore, when the container undergoes rolling and tilting the center of gravity of the container is moved little, so that the container does not easily fall down. Even if the container falls down, the gellan gum continues to supply water to the flowers. Additionally, when the container containing the gellan gum gel undergoes rolling during its transportation, no water is flowed out and little water is evaporated because of the reduced fluidity of the gel surface. A satisfactory water supply is ensured, the cut flowers can be stably held in an erect state by the gel. Since the flowers do not easily fall down, there is eliminated the damage of the flowers resulting from the fall-down.

The cut flowers transporting and preserving methods using the gellan gum are very useful for transporting cut flowers to and from remote locations, and for displaying the same for a long time. Additionally, disposal of the container after the cut flowers are used is very easy for those persons engaging in the flower business, such as natural flower cultivators and flower distributors, and for flower consumers.

What is claimed is:

1. An agent for keeping cut flowers fresh comprises a polysaccharide gel, said gel comprising polysaccharide formed by polymerizing units of →3)-β-D-glucopyranose (Glcp)-(1→4) -β-D-glucuronic acid (GlcpA)-(1→4)-β-D-glucopyranose (Glcp)-(1→4)-α-L-rhamnopyranose (Rhap)-(1→, dispersed at a concentration of 0.05 wt. % to 1.50 wt. % in water, thereby being gelatinized, the resultant polysaccharide gel having a gel strength of 50 to $7000 \times 10^3$ dyn/cm$^2$.

2. The agent for keeping cut flowers fresh according to claim 1, in which the concentration of the polysaccharide is within the range of 0.15 wt. % to 0.50 wt. %, and gel strength thereof is within the range between 100 to $1000 \times 10^3$ dyn/cm$^2$.

3. An agent for keeping cut flowers fresh comprises a polysaccharide gel, said gel comprising polysaccharide formed by polymerizing units of →3)-β-D-glucopyranose (Glcp)-(1→4) -β-D-glucuronic acid (GlcpA)-(1→4)-β-D-glucopyranose (Glcp)-(1→4)-α-L-rhamnopyranose (Rhap)-(1→, dispersed at a concentration of 0.05 wt. % to 1.50 wt. % in water, thereby being gelatinized, the resultant polysaccharide gel having a gel strength of 50 to $7000 \times 10^3$ dyn/cm$^2$, wherein the polysaccharide gel contains a plant life prolonging agent containing at least one member selected from the group consisting of bactericide, nutrient, anti-ethylene agent, growth regulators, and physiological activating agent.

4. The agent for keeping cut flowers fresh according to claim 3, in which the concentration of the polysaccharide is within the range of 0.15 wt. % to 0.50 wt. %, and gel strength thereof is within the range between 100 to $1000 \times 10^3$ dyn/cm$^2$.

5. The agent for keeping cut flowers fresh according to claim 3, in which the polysaccharide gel is contained in a hydrophobic bag or box with an opening allowing cut flowers to be inserted into the polysaccharide gel.

6. The agent for keeping cut flowers fresh according to claim 1, in which the polysaccharide gel is hermetically contained in a hydrophobic bag or box with an opening allowing cut flowers to be inserted into the polysaccharide gel therethrough.

7. A method for preserving cut flowers in a fresh state wherein polysaccharide, which is formed by polymerizing units of →3)-β-D-glucopyranose (Glcp) -(1→4)-β-D-glucuronic acid (GlcpA)-(1→4)-β-D-glucopyranose (Glcp)-(1→4)-α-L-rhamnopyranose (Rhap)-(1→, dispersed at a concentration of 0.05 wt. % to 1.50 wt. %, into water, thereby forming polysaccharide gel of 50 to $7000 \times 10^3$ dyn/cm$^2$ in gel strength, filling a hydrophobic bag or container with the thus prepared polysaccharide gel, and inserting cut ends of the cut flowers, for preservation, into the polysaccharide gel.

8. The method for preserving cut flowers in a fresh state according to claim 7, in which the concentration of the polysaccharide is within the range of 0.15 wt. % to 0.50 wt. %, and the gel strength thereof is within the range between 100 to $1000 \times 10^3$ dyn/cm$^2$.

9. The method for preserving cut flowers in a fresh state according to claim 7, in which the polysaccharide gel contains a plant life prolonging agent containing at least one member selected from the group consisting of bactericide, nutrient, anti-ethylene agent, growth regulators, and physiological activating agent.

10. The method for preserving cut flowers in a fresh state according to claim 7, in which the polysaccharide gel prepared such that the concentration of the polysaccharide is within the range of 0.15 wt. % to 0.50 wt. %, and the gel strength thereof is within the range between 100 to $1000 \times 10^3$ dyn/cm$^2$, is contained in a hydrophobic bag or box, the cut ends of the cut flowers are inserted into the polysaccharide gel, and the cut flowers are preserved in the fresh state.

11. A method of transporting cut flowers in a fresh state wherein polysaccharide, which is formed by polymerizing units of →3)-β-D-glucopyranose (Glcp)-(1→4)-β-D-glucuronic acid (GlcpA)-(1→4)-β-D-glucopyranose (Glcp)-(1→4)-α-L-rhamnopyranose (Rhap)-(1→, dispersed at a concentration of 0.05 wt. % to 1.50 wt. %, into water, thereby to be gelatinized, and the resultant polysaccharide gel has a gel strength of 50 to $7000 \times 10^3$ dyn/cm$^2$, a hydrophobic bag or container is filled with the thus prepared polysaccharide gel, the cut ends of the cut flowers are inserted into the polysaccharide gel contained, and the cut flowers are transported in the fresh state.

12. The method of transporting cut flowers in a fresh state according to claim 11, in which the concentration of the polysaccharide is within the range of 0.15 wt. % to 0.50 wt. %, and the gel strength thereof is within the range between 100 to $1000 \times 10^3$ dyn/cm$^2$.

13. The method of transporting cut flowers in a fresh state according to claim 11, in which the polysaccharide gel contains a plant life prolonging agent containing at least one member selected from the group consisting of bactericide, nutrient, anti-ethylene agent, growth regulators, and physiological activating agent.

14. The method of transporting cut flowers in a fresh state according to claim 11, in which the polysaccharide gel prepared such that the concentration of the polysaccharide is within the range of 0.15 wt. % to 0.50 wt. %, and the gel strength thereof is within the range between 100 to $1000 \times 10^3$ dyn/cm$^2$, is contained in a hydrophobic bag or box, the cut ends of the cut flowers are inserted into the polysaccharide gel, and the cut flowers are transported in the fresh state.

\* \* \* \* \*

UNITED STATES PATENT AND TRADEMARK OFFICE
CERTIFICATE OF CORRECTION

PATENT NO.  : 5,580,975
DATED       : December 3, 1996
INVENTOR(S) : Tada

It is certified that error appears in the above-indentified patent and that said Letters Patent is hereby corrected as shown below:

Title page,
item [73] Assignee, insert the name of the second assignee as follows:

Fushimi Pharmaceutical Co., Limited
Kagawa-ken, Japan

Signed and Sealed this

Twenty-first Day of October 1997

*Attest:*

BRUCE LEHMAN

*Attesting Officer*     *Commissioner of Patents and Trademarks*